United States Patent [19]

Meyers

[11] 3,965,125

[45] June 22, 1976

[54] SYNTHESIS OF CERTAIN BIS(PHTHALIC ANHYDRIDES)

[75] Inventor: Robert A. Meyers, Los Angeles, Calif.

[73] Assignee: TRW Inc., Redondo Beach, Calif.

[22] Filed: Feb. 8, 1971

[21] Appl. No.: 113,747

[52] U.S. Cl. .......................... 260/346.3; 260/251 R; 260/152; 260/287 R
[51] Int. Cl.$^2$ ......................................... C07D 307/89
[58] Field of Search ............. 260/346.3, 152, 251 R, 260/326 N

[56] References Cited
UNITED STATES PATENTS 3,431,240   3/1969   Vogel et al. .................... 260/346.3

Primary Examiner—Henry R. Jiles
Assistant Examiner—Bernard Dentz
Attorney, Agent, or Firm—Daniel T. Anderson; Alan D. Akers; Edwin A. Oser

[57] ABSTRACT

Monomeric high molecular weight dianhydrides or tetraacids can be produced by the nucleophilic coupling of a halo substituted phthalimides acid and an aliphatic or aromatic compound having polyfunctional groups capable of reacting with the halo moiety of the phthalinide followed by hydrolysis and dehydration. Specifically, 4-chlorophthalate sodium salt is converted to an imide to reduce side reactions with the carboxylic acid groups prior to reaction with 4,4'-disodiumdiphenylene oxide sulfone or 2,2-di (4-sodium phenoxide) propane. After the reaction of the imide and the sulfone or propane compounds, the diimide formed is converted to the corresponding dianhydride.

6 Claims, No Drawings

SYNTHESIS OF CERTAIN BIS(PHTHALIC ANHYDRIDES)

Generally, when high performance polymers are sought, high molecular weight compounds are the first investigated. These high molecular weight compounds offer the best known overall characteristics of thermal stability, chemical stability, and physical strength.

Copending patent application Ser. No. 799,106, filed Feb. 13, 1969 and now abandoned, discloses a high molecular weight cyclic compound and a method of making the compound. While the cyclic compound, bis (3,4-dicarboxyphenoxyphenyl) sulfone exhibits several attractive properties, the proposed method of making the sulfone compound disclosed in the application is expensive. The method proposed for making the sulfone compound involves the reaction between 3,4-xylenol and p,p'-dichlorodiphenyl sulfone, both expensive starting materials which give a low yield product.

Now it has been discovered that high molecular weight dianhydride terminated monomers can be made by the nucleophilic substitution reactions of a functionally ortho substituted benzene acid and an aliphatic or aromatic compound having polyfunctional groups capable of reacting with the functional ortho group on the benzene acid. More specifically, high molecular weight dianhydride terminated monomers can be made by reacting a substituted phthalimide characterized by the formula:

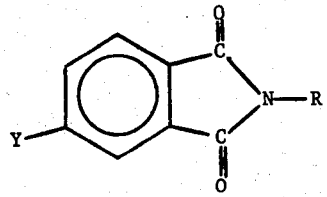

wherein Y is a functional group selected from the group consisting of —Cl, —F, —Br, and —I and R is selected from the group consisting of $C_1$ to $C_5$ alkyl groups, phenyl, and substituted phenyl, such as chlorophenyl or nitrophenyl, with a polyfunctional compound characterized by the formula:

A — Z — A wherein A is a functional group capable of reacting with the Y group on the pthalimide and is selected from the group consisting of —OLi, —ONa, —OK, —SLi, —SNa, —SK, —NHR' wherein R' is a phenyl or a $C_1$ to $C_6$ alkyl group, and —NH$_2$ and Z is selected from the group consisting of an aliphatic or an aromatic group to form a diimide terminated aliphatic or aromatic intermediate, and then converting the diimide formed to the corresponding dianhydride. Preparation of the dianhydride product requires pre-preparation of the reactants from commercially available starting materials. In the pre-preparation, the preferred starting materials are monosodium-4-chlorophthalate and 4,4'-dihydroxydiphenyl sulfone or 2,2-di(4-hydroxyphenyl) propane. The chlorophthalate is converted to the corresponding imide to reduce undersirable side reactions prior to reaction with the aromatic sulfone or propane compound.

PREPARATION OF 4-CHLOROPHTHALIMIDE

Preparation of the preferred end caps begins with monosodium-4-chlorophthalate. Monosodium-4-chlorophthalate is water insoluble and is a commercially available material used in the dye industry. Monosodium 4-chlorophthalate is converted to the acid by reaction with concentrated sulfuric acid at room temperature according to the following:

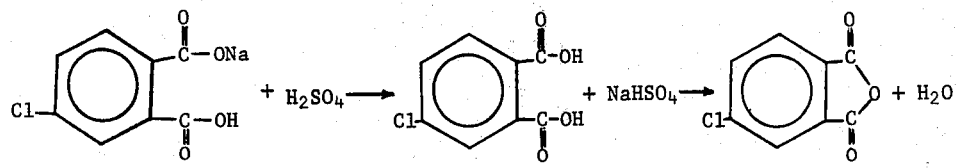

the reaction is carried out on a substantially equal mole ratio, and the acid product is extracted with ether and then converted to the anhydride by heating 2 hours at approximately 150°–170°C. Because the anhydride group has a reactive strength close to that of the chloride group for highly basic and nucleophilic salt reactants, the anhydride is converted to a less reactive imide group by a substantially equal mole ratio reaction with a primary amine refluxed in solvent according to the following:

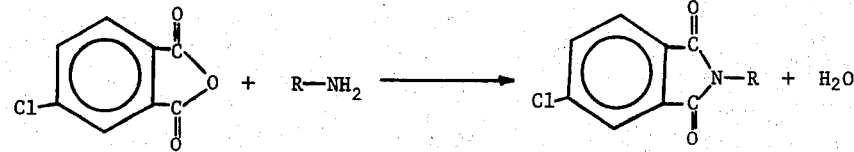

where R represents a phenyl or a lower alkyl group, $C_1$ – $C_5$, preferably phenyl. In the imide form, the chloride group becomes the preferred reaction site whereby satisfactory yields may be obtained without undue quantities of side products being formed. Of course, similar results may be obtained by starting with a functionally substituted benzoic acid and reacting them to the corresponding amide.

PREPARATION OF THE FUNCTIONALLY TERMINATED ALIPHATIC OR AROMATIC COMPOUND

The functionally terminated aromatic or aliphatic compound is prepared by reacting a polyhydroxy or a polymercapto compound with an alkali metal or an alkali metal compound to produce an aromatic or aliphatic compound capable of reacting with the functional group on the benzene acid. Also, polyamino terminated aromatic or aliphatic compounds can be reacted directly. Dihydroxy cyclic compounds, such as 4,4'-dihydroxydiphenyl sulfone and 2,2-di(4-hydroxyphenyl) propane are preferred commercially available starting materials. These aromatic compounds are reacted with two moles of alkali metal hydroxide, preferably sodium hydroxide, to one mole of aromatic compound in an aqueous solution. A 40% aqueous - methanol solution is preferred, however, if no methanol is present, the reaction will still proceed, but at a much slower rate.

A few of the many compounds suitable for use in this invention may be selected from the following:

TABLE

| | |
|---|---|
| 1,5-dihydroxyanthraquinone | dihydroxynaphthalene |
| 1,4-dihydroxyanthraquinone | 2,2'dihydroxy-4,4'dimethoxy-benzophenone acid |
| 1,8-dihydroxyanthraquinone | 1,3-dihydroxypropane |
| 2,4-dihydroxybenzophenone | 1,3-dihydroxy-2-propanone |
| 1,3-dihydroxybutane | 4,6-dihydroxypyrimidine |
| 1,4-dihydroxybutane | 2,4-dihydroxyquinoline |
| 1,3-dihydroxy-4-chlorobenzene | hydroquinone |
| $\beta\beta'$-dihydroxydiethyl ether | ethylene glycol |
| 2,2'-dihydroxydiphenyl | resorcinol |
| di($\beta$-hydroxyethyl)aniline | 4,4'-isopropylidenediphenol |
| $\beta\beta'$-dihydroxyethyl ether | dihydroxybenzoquinone |
| 4,4'-isopropylidenebis(2,6-dibromophenol) | 1,5-dihydroxy-1,2,3,4-tetra hydronaphthalene |
| 2,4-dihydroxy-1,4-benzidine | 1,4-dihydroxy-4,4'-dinitroanthraquione |
| 1,8-dihydroxy-4,4'-dinitroanthraquinone | 2,4-dihydroxy-6-methylpyrimidine |
| 6,7-dihydroxytropinone | 4,4'-dihydroxyazobenzene |
| 1,3-dihydroxypropane | 4,4'-diamino diphenyl propane |
| 1,2-ethanedithiol | 1,5-diamino naphthalene |
| phenylene diamine | 4,4'-diamino diphenyl ether |
| benzidine | 4,4'-diamino diphenyl-N-phenyl amine |
| 4,4'diamine benzophenone | |

NUCLEOPHLIC COUPLING

The nucleophilic substitution coupling reaction is carried out in an aprotic and highly polar solvent. Hexamethylphosphoramide, dimethylsulfoxide, dimethylformamide, and dimethyl acetamide are suitable solvent media for the nucleophilic reaction, however, hexamethylphosphoramide gave the most pure product in the shortest time with dimethylacetamide being the next preferred for the sulfone compound. Dimethylformamide gave the best results when used as the solvent medium for the coupling reaction of the propane compound. The nucleophilic coupling reaction using two moles of 4-chlorophthalimide to one mole of sulfone was completed in about 47 hours at a temperature of 150°C in hexamethylphosphoramide. The same coupling reaction using dimethylacetamide required about 111 hours at 155°C while the use of dimethylformamide required approximately two weeks because the temperature could not be raised above 140°C without solvent decomposition. By contrast, the coupling reaction using two moles of 4-chlorophthalimide to one mole of the propane compound was complete in 140 hours at 130°C using dimethylformamide. Obviously, the particular solvent to be used with each cyclic compound will vary, and accordingly, solvents other than these three suggested may be necessary. Selection of the solvent should be made on its high polar and nucleophilic reaction promoting characteristics.

After the nucleophilic substitution, the resulting diimide is hydrolyzed to the corresponding acid compound. Hydrolysis of primary aromatic amines occurs more readily than hydrolysis of primary aliphatic amines, and therefore, aniline or aniline with ortho or para substituted electron drawing groups such as o- or p- nitroaniline, or o- or p-haloaniline are preferred. Hydrolysis of the diimide produced from primary aromatic amines is effected by reaction with sodium hydroxide to produce the corresponding tetraacid.

Dehydration of the tetraacid to form the corresponding dianhydride is accomplished by heat staging. Dehydration by heat staging involves placing the tetraacid in an oven under vacuum and gradually raising the temperature from room temperature to about 180°C over an 8 to 20 hour period. Heat staging is preferred to simply heating the tetraacid at the maximum temperature because the tetraacid has a tendency to polymerize and form an undesirable coherent mass if the temperature is not raised gradually.

While primary aliphatic amines can be used for the production of the diimide intermediate, hydrolysis of the aliphatic diimide is difficult and the purity of the dianhydride product is poor. Therefore, in order to render the aliphatic diimide more readily available for hydrolysis, the diimide may be reacted with aqueous hydrazine to form the corresponding dihydrazide which will undergo hydrolysis more readily.

The dihydrazide can be hydrolyzed in either of two ways. The first way effects the oxidation by reaction with an excess, e.g., 8 to 30 moles, of concentrated nitric acid to one mole of the dihydrazide at room temperature. When the addition is complete, the reaction mixture is stirred for an additional time usually about 2 hours, to insure complete reaction. At the end of that time, the mixture is diluted with an excess of water, filtered, and dried.

In the alternate method, an excess of potassium permanganate in an alkali metal hydroxide, usually containing about 2 to 3 moles of potassium permanganate and 4 to 5 moles of sodium hydroxide, is added to the dihydrazide. Upon completion of the reaction, a dilute solution of nitric acid is added to neutralize the excess base. Solid tetraacid is filtered and dried in vacuum at slightly elevated temperatures.

Dehydration of the tetraacid to the corresponding dianhydride can be accomplished in either of two ways, also. The dehydration of the tetraacid may be achieved by heat staging described previously or by reaction with acetic anhydride. When reaction with acetic anhydride is used, the tetraacid is refluxed for 20 to 30 minutes with an excess of acetic anhydride. The hot solution is treated then with activated charcol and filtered while hot. A solid crystalline anhydride product precipitates out of solution upon cooling of the filtrate. Subsequent recrystallization in acetic anhydride further purifies the product.

So that the present invention may be more clearly understood, the following examples disclose some of the preferred, but not necessarily the only, methods of making the dianhydrides of this invention.

EXAMPLE I

To a suspension of 750 g of monosodium-4-chlorophthalate and 1200 ml water was added 120 ml conc. sulfuric acid. The resulting brown solution was extracted with three 400 ml portions of ether. The combined extracts were treated with carbon black, filtered and the ether distilled. The 4-chlorophthalic acid obtained was dehydrated by heating to 170°C for two hours to give 548 g of anhydride. To a solution of the anhydride in 2250 ml of xylene was added 279 g of aniline diluted with an equal weight of xylene. The solution was refluxed for 16 hours and the water formed was collected in a Dean-Stark trap. After treatment with carbon black the hot xylene solution was cooled to 5°C to give 475 g of crude 4-chloro-N-phenyl phthalimide. Recrystallization from 2000 ml toluene, twice, provided 364 g of 92% pure imide.

To 500.6 g of 4,4'-dihydroxydiphenylsulfone in 1000 ml of 40% aqueous methanol was added a solution of 168 g sodium hydroxide in 500 ml 40% aqueous methanol. After removing the solvent at reduced pressure, 570 g of disodium salt was obtained.

A 41.3 g portion of 4-chloro-N-phenylphthalimide and 90 g of dimethyl acetamide (DMAC) were introduced into a 250 ml three necked round bottom flask equipped with magnetic stirring bar, condenser, thermometer and gas inlet. The temperature was adjusted to 150°C and 22 g of disodium dihydroxydiphenyl sulfone was added. The reaction was 94% complete after 192 hours and was decomposed by pouring it into 600 ml ice water. Approximately 45.2 g of crude diimide was extracted with acetone to give a white-yellow solid melting at 288°-293°C.

Hydrolysis of the diimide was effected by refluxing for 48 hours, approximately 27.6$_g$ of diimide in a solution of 8g of sodium hydroxide dissolved in 64g of water. After the refluxing was complete, the solution was acidified with 2N nitric acid to yield 22 g of crude tetraacid. The tetraacid was recrystallized to yield 19.4 g of tetraacid.

Approximately 18.4g of tetraacid was dehydrated by gradually heating to 180°C under vacuum over an eighteen hour period to form the dianhydride. Approximately 16.9 g of crude dianhydride was leached with water to give 15.4g of a product having a melting point range of 250°-254°C.

EXAMPLE II

To a suspension of 750 g of monosodium-4-chlorophthalate and 1200 ml water was added 120 ml conc. sulfuric acid. The resulting brown solution was extracted with three 400 ml portions of ether. The combined extracts were treated with carbon black, filtered and the ether distilled. The 4-chlorophthalic acid obtained was dehydrated by heating to 170°C for two hours to give 550 g of anhydride. To a solution of the anhydride in 600 ml of toluene was added 219 g of n-butylamine diluted with an equal weight of toluene. The solution was refluxed for 16 hours and the water formed was collected in a Dean-Stark trap. After treatment with carbon black the hot toluene solution was cooled to 5°C to give 280 g of crude 4-chloro-N-butyl phthalimide. Recrystallization from 1000 ml ethanol afforded 240 g of 99% pure imide.

To 500.6 g of 4,4'dihydroxydiphenylsulfone in 100 ml of 40% aqueous methanol was added a solution of 168 g sodium hydroxide in 500 ml 40% aqueous methanol. After removing the solvent at reduced pressure 570 g of disodium salt was obtained.

A 175 g portion of 4-chloro-N-butylphthalimide and 418 g of hexamethylphosphoramide (HMPA) were introduced into a 2 liter three necked round bottom flask equipped with magnetic stirring bar, condenser, thermometer and gas inlet. The temperature was adjusted to 150°C and 107 g of disodium dihydroxydiphenyl sulfone was added. The reaction was 98% complete after 48 hours and was decomposed by pouring it into 1200 ml ice water. The crude diimide (mp 80°-90°C) was recrystallized from isopropanol to give a white solid melting at 128°-131°C.

To a 300 ml round-bottom flask equipped with a stirrer and reflux condenser was added 130 g of diimide and 100 g of 40% aqueous hydrazine. After refluxing for 16 hours the clear solution was added to excess dilute hydrochloric acid to give 111 g of white diphthalhydrazide. Extraction with boiling acetic acid for 12 hours gave material melting at 350°-352°C.

A 140 g portion of diphthalhydrazide was dissolved in a solution of 64 g potassium hydroxide in 1000 ml water. Portionwise 106 g of potassium permanganate was added during one hour. After stirring an additional hour the mixture was warmed to 60°C and the excess permanganate was decomposed with methanol. Manganese dioxide was removed from the reaction by filtration and the basic filtrate was acidified with 2N HNO$_3$ to give 133 g of tetraacid.

The tetraacid was dehydrated by gradually heating the material to 180°C under vacuum over an eighteen hour period. The bis (4-(3,4-dicarboxyphenoxy)phenyl) sulfone dianhydride obtained melts at 248°-252°C.

EXAMPLE III

To 34 g of 4,4'-isopropylidenediphenol (bisphenol A) dissolved in 50 ml methanol was added a solution of 11.9 g sodium hydroxide in 40 ml water. The solvent was removed at reduced pressure to give 37 g of disodium bisphenol A.

A 23.8 g portion of 4-chloro-N-phenylphthalimide as prepared in Example I, was dissolved in 100 ml dry dimethylformamide (DMF) and heated to 130°C under nitrogen atmosphere, then a 136 g portion of disodium bisphenol A was added and the mixture was stirred for 140 hours. The volume was then reduced to 50 ml at reduced pressure and the reaction mixture slowly added to 300 ml ice water. The precipitate was collected, washed and dried to give 32 g of crude imide which was used without further purification in the next step.

To 31.5 g of diimide was added 17 g of 40% aqueous hydrazine and the mixture refluxed for 16 hours. Treatment of the solution with excess dilute hydrochloric acid gave 24.5 g of diphthalhydrazide.

A 21.9 g portion of diphthalhydrazide dissolved in a solution of 10 g potassium hydroxide in 200 ml water was oxidized with 6.8 g potassium permanganate. Manganese dioxide from the reaction was removed by filtration and 20.2g of tetraacid was obtained upon acidification of the filtrate. The desired dianhydride was obtained by thermal dehydration as in Example 1.

EXAMPLE IV

Approximately 14.6 g of crude diimide as prepared in Example 2, were combined in a 400 ml flask with 100 ml of 20% sodium hydroxide and 20 ml of 2-propanol. The solution was refluxed for 48 hours and acidified with 2N nitric acid to yield 12.0 g of tetaacid. The tetraacid was heat-staged as in Example 2 to yield 11.4 g of dianhydride.

The monomers produced by the methods of this invention provide an economical starting material for polyimides, polybenzimidazoles, polypyrrones, and polyquinoxolines. These polymers which have good thermal stability and chemical resistance, offer engineering materials which can meet the severe specifications required of advanced structures.

I claim:

1. A method of making monomeric high molecular weight anhydrides comprising:

A. i. reacting a substituted phthalimide characterized by the formula:

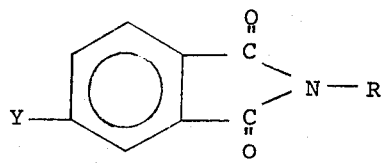

where Y is a functional group selected from the group consisting of —CL, —F, —Br, and —I, and R is selected from the group consisting of $C_1$ to $C_5$ alkyl groups, phenyl, with (ii) a polyfunctional compound characterized by the formula:

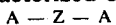

wherein A is a functional group capable of reacting with Y and is selected from the group consisting of —OLi, —ONa, —OK, —SLi, —SNa, —SK, —NHC$_6$H$_5$, —NHCH$_3$, —NHC$_2$H$_5$, —NHC$_3$H$_7$, —NHC$_4$H$_9$, —NHC$_5$H$_{11}$, —NHC$_6$H$_{13}$, and —NH$_2$ and Z is selected from the group consisting of arylene, alkylene, haloarylene, oxyhisaryl, oxlybisaryl, alkylenebisaryl, nitro substituted anthraquinonylene, azabisoryl, alkyl substituted pyrimidylene, and pyrimidylene sulfonebisaryl to form a diimide terminated cyclic intermediate, and B. hydrolyzing and subsequently dehydrating said diimide terminated intermediate to the corresponding dianhydride.

2. A method according to claim 1 wherein the phthalimide is 4-chloro-N-butylphalimide.

3. A method according to claim 1 wherein the polyfunctional compound is 4,4'-disodiumdiphenyloxide sulfone.

4. A method according to claim 1 wherein the polyfunctional compound is 2,2-di(4-sodium phenoxide) propane.

5. A method according to claim 3 wherein the dianhydride product is bis-[4(3,4-dicarboxyphenoxy)phenyl] sulfone dianhydride.

6. A method according to claim 4 wherein the dianhydride product is 2,2-bis[4-(3,4-dicarboxyphenoxy)-phenyl] propane dianhydride.

\* \* \* \* \*